US00PP31400P2

(12) United States Plant Patent
Austin

(10) Patent No.: US PP31,400 P2
(45) Date of Patent: Jan. 28, 2020

(54) ***ROSA HYBRIDA* SHRUB NAMED 'AUSEARNSHAW'**

(50) Latin Name: *Rosa hybrida*
Varietal Denomination: AUSearnshaw

(71) Applicant: David Austin Roses Ltd., Albrighton, Wolverhampton (GB)

(72) Inventor: David J. C. Austin, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 16/350,902

(22) Filed: Jan. 30, 2019

(30) Foreign Application Priority Data

Sep. 21, 2018 (GB) ..... PBR 5/2140

(51) Int. Cl.
*A01H 5/02* (2018.01)
*A01H 6/74* (2018.01)

(52) U.S. Cl.
USPC ..... Plt./107

(58) Field of Classification Search
USPC ..... Plt./107
CPC ..... A01H 5/02; A01H 6/74
See application file for complete search history.

*Primary Examiner* — Annette H Para
(74) *Attorney, Agent, or Firm* — KPPB LLP

(57) ABSTRACT

A variety of rose plant of the shrub class, named 'AUSearnshaw'. The 'AUSearnshaw' is a variety of a rose shrub having a healthy bushy strong upright growth, blooms of a soft pink color with a yellow-apricot center and a button eye, and a strong fragrance that starts as Tea and develops into an Old Rose.

1 Drawing Sheet

Classification: The present invention relates to a new *Rosa hybrida* shrub of the market class 'English Rose'.

Variety denomination: The new plant has the varietal denomination 'AUSearnshaw'.

CROSS-REFERENCE TO RELATED APPLICATION

The present application claims priority to UK Varietal Plant Patent 5/2140, filed Sep. 21, 2018.

ORIGIN OF INVENTION

This invention relates to a new and distinct variety of shrub rose plant named 'AUSearnshaw', which was originated from the cross-pollination of the two 'unnamed' and unpatented seedlings of *Rosa hybrida.*

BACKGROUND OF THE INVENTION

The primary objective of this breeding was to produce a bushy rose variety having a strong, healthy upright growth with distinctive blooms, which are neat and rather flat, each bloom being a lovely soft pink with a yellow-apricot center with a button eye, and having a strong fragrance with begins as Tea and becomes Old Rose.

SUMMARY OF THE INVENTION

Among the features which distinguish the new variety from others presently available and commercial rose cultivars known to the inventor is the following combination of characteristics: a healthy bushy shrub with strong upright growth, blooms of a soft pink color with a yellow-apricot center and a button eye, and a strong fragrance that starts as Tea and develops into an Old Rose.

Asexual reproduction of the new variety by budding as performed at Bowling Green Lane in Albrighton, Britain shows that the foregoing and other distinguishing characteristics come true to form and are established and transmitted through succeeding asexual propagations. 'AUSearnshaw' may be asexually propagated by budding. The budding successfully occurred on an unpatented plant/rootstock *Rosa dumetorum* 'Laxa' for the observed plants.

COMPARISON WITH PARENTS

The maternal and paternal parents of 'AUSearnshaw' are two unnamed seedlings. The new rose may be distinguished from its maternal parent, by the following combination of characteristics: the maternal parent is a shorter bush and has uniformly deep pink flowers compared to the soft pink, apricot-centered blooms of 'AUSearnshaw'. The new rose may be distinguished from its pollen parent, by the following combination of characteristics: the paternal parent has a larger growth and its blooms are more cupped with fewer petals than 'AUSearnshaw'.

COMPARISON WITH THE CLOSEST COMMERCIALLY AVAILABLE CULTIVAR

The closest commercially available cultivar to the new variety is the 'AUSrimini' (U.S. Plant Pat. No. 18,716). While the color of both are a similar soft pink, the new rose may be distinguished from the 'AUSrimini' based on the apricot-colored center of 'AUSearnshaw'. It may also be distinguished by the fact that the growth habit differs in that 'AUSrimini' is a short climber whereas 'AUSearnshaw' is a shrub.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of budded 'AUSearnshaw' specimens were made at the nursery at David Austin Roses Limited in Albrighton, Wolverhampton, United Kingdom. The following description is of 4 year-old rose plants of the new variety grown in a garden environment in Albrighton, Britain in the month of June. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

*Size*.—About 2 cm long and 1.8 cm in diameter when the petals start to unfurl.

*Form*.—The bud form is pointed ovoid and broad-based.

*Color*.—When sepals first divide, the bud color is RHS 38B (red group) with RHS 67A (red-purple group) and RHS 157A (green-white group). When half blown, the upper sides of the petals are RHS 69B (red-purple group), and the lower sides of the petals RHS 69B (red-purple group).

*Calyx*.—Shape: opens to a star shape, with the sepals finally folding back against the stems. Length: 6.2 cm. Diameter: 1.3 cm.

*Sepals*.—Arrangement: Regularly arranged. Color: Upper Surface: RHS 145B (yellow-green group). Lower Surface: RHS 144C (yellow-green group) with RHS 186A (grayed-purple group). Length: 2.9 cm. Width: 1 cm. Shape: Lanceolate. Surface texture: Upper Surface: Downy. Lower Surface: Smooth. Number: There are 3 lightly appendaged sepals, and 2 unappendaged sepals with hairy edges. Sepal Extensions: Are medium.

*Receptacles*.—Color: RHS 144C (yellow-green group) with RHS 186A (grayed-purple group). Shape: Funnel. Size: Broad, about 1 cm long×1 cm wide. Surface: Smooth.

*Peduncle*.—Length: Medium, averaging about 8 cm. Surface: Glandular. Color: RHS 144C (yellow-green group) with some RHS 186A (grayed-purple group). Strength: Strong.

Blooms:

*Size*.—Large, average open diameter is about 9 cm.

*Borne*.—Several together, with the florescence having a rounded shape.

*Stems*.—Strength: Strong, average length is about 40 cm. Diameter: 5 mm.

*Form*.—When first open, bloom is cupped. Permanence of bloom: flattens.

*Flower type*.—Double.

Petalage: Number of petals under normal conditions: 106.

*Color*.—The upper sides of the petals are RHS 69D (red-purple group). The upper sides of the inner petals are RHS 9D (yellow group). The reverse sides of the petals are RHS 69D (red-purple group). The base of the petals has a yellow spot that is RHS 9B (yellow group).

*Variegations*.—None.

*Discoloration*.—The general tonality at the end of the first day is RHS 69D (red-purple group), and at the end of the third day is RHS 155C (white group).

*Fragrance*.—Strong. Character of fragrance: Tea developing to Old Rose.

Petals:

*Texture*.—Smooth.

*Size*.—Width: 2.3 cm. Length: 4 cm.

*Surface*.—Smooth.

*Shape*.—Obovate.

*Margin*.—Entire with medium undulations which are in the nature of frilling.

*Apex shape*.—Rounded, slightly cuspidate.

*Base shape*.—Pointed.

*Form*.—Slightly incurved.

*Arrangement*.—Regular, with a button eye.

*Petaloids*.—Number: Around 50. Color: RHS 18C (yellow-orange group). Length: 2 cm. Width: 1 cm. Shape: Obovate. Margin: Entire.

*Persistence*.—Petals drop off cleanly before drying.

*Lastingness*.—On the plant: Short about 4 days. As a cut flower: not tested.

Reproductive parts:

*Stamens*.—Number: approximately 35. Length: 8-9 mm.

*Anthers*.—Length: 2 mm. Color: RHS 17B (yellow-orange group). Arrangement: Mixed with petaloids.

*Filaments*.—Color: RHS 17B (yellow-orange group). Length: 7-8 mm.

*Pollen*.—Color: RHS 17A (yellow-orange group). Amount: Moderate.

*Pistils*.—Number: 85. Length: approximately 9 mm.

*Styles*.—Color: RHS 150D (yellow-green group). Length: between 7-8 mm.

*Stigmas*.—Color: RHS N66B (red-purple group). Length: approximately 1.5 mm.

*Hips*.—NONE Observed.

PLANT CHARACTERISTICS

Plant form: Shrub.

Plant growth: Very vigorous and upright.

Age to maturity: 2 years.

Mature plant: Height: 1 m 40 cm. Width: 1 m 20 cm.

Rootstock: *Rosa dumetorum* 'Laxa' for the observed plants.

Foliage:

*Number*.—Leaflets on normal mid-stem leaves is: 5 mostly (some 3 or 7) (including terminal leaflet).

*Size*.—Large, about 15 cm long×12 cm wide.

*Quantity*.—Abundant. Number of leaves per flowering stem is: 10.

*Color*.—New foliage: Upper side: RHS 144A (yellow-green group) with RHS 185B (grayed-purple group). Lower side: RHS 185B (grayed-purple group) with RHS 144A (yellow-green group). Old foliage: Upper side: RHS 137A (green group). Lower side: RHS 146B (yellow-green group).

Leaflets:

*Size*.—About 6 cm long×4 cm wide.

*Shape*.—Pointed oval.

*Base shape*.—Cordate.
*Apex shape*.—Acute.
*Texture*.—Leathery.
*Glossiness*.—Strong.
*Edge*.—Serrated.
*Serrations*.—Single and large.
*Petiole*.—Color: RHS 144A (yellow-green group) with some shading of RHS 185B (grayed-purple group). Length: 4.5-5 mm. Width: 1.5 mm. Surface Texture: Smooth, with prickles on underside.
*Petiole rachis*.—Color: RHS 144A (yellow-green group) tinged with some shading of RHS 185B (grayed-purple group). Underside: with prickles.
*Stipules*.—Length: 2.6 cm, glandular. Color: RHS 144A (yellow-green group).
*Auricle*.—Shape: Lanceolate. Length: 9 mm. Width: 2 mm. Color: RHS 144A (yellow-green group).
*Vein color*.—Color: RHS 137A (green group).
*Venation pattern*.—Reticulate.

Wood:
*New wood*.—Color: RHS 185B (grayed-purple group). Bark: Smooth.
*Old wood*.—Color: RHS 137A (green group). Bark: Smooth.

Branching habit:
*Number*.—12.
*Dimensions*.—Length: 60 cm. Diameter: 6 mm.

Stems:
*Mature stem*.—Length: 50 cm. Diameter: 6-7 mm.
*Internode distance*.—6 cm. The above measurements are all variable, depending on growing conditions in a season.
*Stem pubescence present*.—No.

Prickles:
*Quantity*.—On main canes from base: Ordinary. Number per stem length: 10 per 20 cm. On laterals from main canes: Ordinary. Number per stem length: 10 per 20 cm.
*Form*.—Deep concave.
*Length*.—5 mm.
*Color when young*.—RHS 185B (grayed-purple group).
*Color when mature*.—RHS 185B (grayed-purple group).

Small prickles:
*Quantity*.—Main stalk: Medium. Number per stem length: 10 per 20 cm. Laterals: Medium. Number per stem length: 10 per 20 cm.
*Color*.—When young: RHS 185B (greyed-purple color). When mature: RHS 185B (greyed-purple color).

Disease resistance:
*Powdery mildew* (*Podosphaera pannosa*).—Resistant.
*Downy mildew* (*Peronospora species*).—Resistant.
*Blackspot* (*Diplocarpon rosae*).—Resistant.
*Rust* (*Phragmidium tuberculatum*).—Resistant.

Pest resistance: Not tested.
Winter hardiness: Not tested.
Growing conditions: Normal garden conditions.

What is claimed is:

1. A new and distinct variety of rose plant of the shrub class, substantially as herein shown and described.

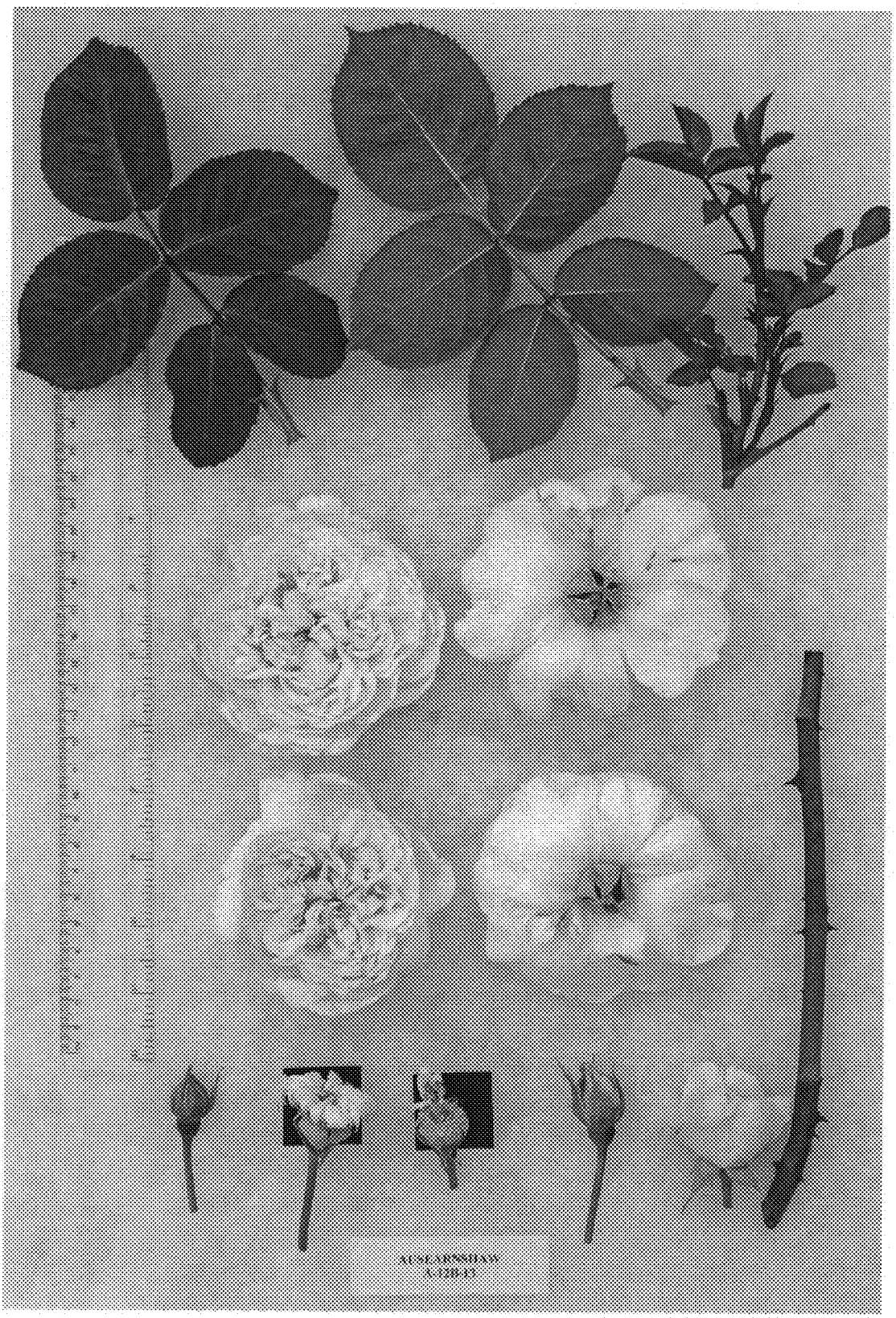

* * * * *